United States Patent [19]

Suzuki et al.

[11] Patent Number: 5,451,339
[45] Date of Patent: Sep. 19, 1995

[54] LIQUID CRYSTAL MONOMERIC COMPOUND AND LIQUID CRYSTAL POLYMER COMPOUND MODIFIED THEREWITH

[75] Inventors: Yoshiichi Suzuki; Yoshio Imai, both of Tokyo; Masaaki Kakimoto, Yokohama, all of Japan

[73] Assignee: Showa Shell Sekiyu Kabushiki Kaisha, Tokyo, Japan

[21] Appl. No.: 63,562

[22] Filed: May 19, 1993

[30] Foreign Application Priority Data

May 20, 1992 [JP] Japan ................... 4-152885

[51] Int. Cl.⁶ .................. C09K 19/52; C09K 19/20; C09K 19/12; C07F 7/04
[52] U.S. Cl. ................. 252/299.01; 252/299.66; 252/299.67; 252/299.62; 252/299.65; 428/1; 556/434
[58] Field of Search .............. 252/299.66, 299.62, 252/299.67, 299.01; 428/1; 556/434

[56] References Cited

U.S. PATENT DOCUMENTS

| | | | |
|---|---|---|---|
| 4,358,391 | 11/1982 | Finkelmann et al. | 252/299.01 |
| 4,844,835 | 7/1989 | Uchida et al. | 252/299.01 |
| 4,864,033 | 9/1989 | Bradshaw et al. | 558/446 |
| 4,913,839 | 4/1990 | Uchida et al. | 252/299.01 |
| 4,918,213 | 4/1990 | Nohira et al. | 558/271 |
| 4,954,600 | 9/1990 | Hachiya | 528/89 |
| 5,073,306 | 12/1991 | Nohira et al. | 252/299.61 |
| 5,110,498 | 5/1992 | Suzuki et al. | 252/299.66 |
| 5,138,010 | 8/1992 | Keller et al. | 528/26 |
| 5,141,668 | 8/1992 | Nishiyama et al. | 252/299.62 |
| 5,167,861 | 12/1992 | Suzuki et al. | 252/299.65 |
| 5,212,027 | 5/1993 | Etzbach et al. | 430/20 |
| 5,252,695 | 10/1993 | Niciri et al. | 528/30 |
| 5,269,963 | 12/1993 | Uchida et al. | 252/299.01 |
| 5,271,866 | 12/1993 | Uchida et al. | 252/299.01 |

FOREIGN PATENT DOCUMENTS

| | | |
|---|---|---|
| 0362714 | 4/1990 | European Pat. Off. |
| 0833615 | 4/1990 | European Pat. Off. |
| 0435240 | 7/1991 | European Pat. Off. |
| 0478387 | 4/1992 | European Pat. Off. |
| 0529597 | 3/1993 | European Pat. Off. |
| 9201764 | 2/1992 | Germany |
| 1099025 | 4/1989 | Japan |
| 3068686 | 3/1991 | Japan |
| 4031405 | 2/1992 | Japan |

OTHER PUBLICATIONS

61st Annual Seminar, Chemical Society of Japan.

Primary Examiner—Robert L. Stoll
Assistant Examiner—C. Harris
Attorney, Agent, or Firm—Cushman Darby & Cushman

[57] ABSTRACT

The present invention is to provide a liquid crystal monomeric compound where a liquid crystal phase readily appears, which is excellent in alignment control, film-formability, durability, heat-stability and compatibility, and is able to be applied to electro-optical liquid crystal elements and recording elements; and a side-chain liquid crystal polymer compound modified with such a monomeric compound.

The liquid crystal monomeric compound is represented by the following formula:

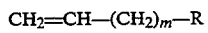

[1]

wherein m is an integer of 2 to 20 and R is a group selected from the group consisting of

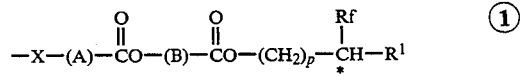

wherein p is 1 or 2, Rf is $CF_3$ or $CF_2F_5$, $R^1$ is an alkyl group having 3–18 carbon atoms, * means an optically active carbon atom, (A) and (B) each is a group independently selected from the group consisting of

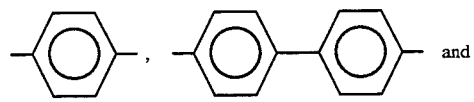

-continued
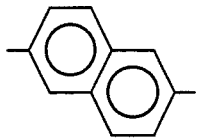
which may be substituted with one or more halogen atoms, and X is —O—, —COO— or a direct linkage, and
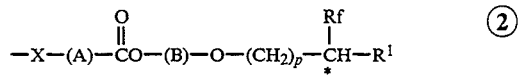
wherein p, Rf, R$^1$, (A), (B), X and * have the same meanings as above.
2 Claims, No Drawings

LIQUID CRYSTAL MONOMERIC COMPOUND AND LIQUID CRYSTAL POLYMER COMPOUND MODIFIED THEREWITH

The present invention relates to a novel monomeric compound and also to a side-chain liquid crystal polymer compound modified therewith. A film having molecular alignment is produced from the polymer by an aligning treatment. The present polymer compounds cause reversible change in, for example, electric fields as same as low molecular weight liquid crystals, so that they are applied to display elements, recording elements, electro-optical devices and nonlinear optical materials. Furthermore, the present compounds have so superior film-processability that film displays having a large area and a curved screen are easily produced.

Conventional liquid crystal display elements are electro-optical devices using mainly lower molecular weight liquid crystals. Driving systems such as TN, twisted TN and ferroelectric liquid crystal systems have been proposed, and a part of which is now in practice. However, liquid crystal displays driven by a TN or STN system are hardly applicable to high speed driving softs, since they have response speed as slow as a few ten millisecondsand narrow viewing angle. A driving system using ferroelectric liquid crystals encounters a mountain of difficulties in practice, although the system is considered to make it possible to built large and high quality displays taking advantage of its high speed response and good memory.

Side-chain high molecular liquid crystal polymers are of high molecular skeleton structure to which a mesogen group is bonded through flexible spacers. They are self-supportable and are ready to form a film. Large display screens are able to be prepared using the compounds and curved surfaces of display screens containing the compounds are easily worked.

A few displays using liquid crystal polymers are proposed, such as nematic type, cholesteric type and ferroelectric type. However, they have a number of problems to be solved yet for practical purposes, that is, (i) unpractical response speed as low as a few hundred milliseconds because of their higher viscosity than that of low molecular liquid crystal, (ii) unevenness in alignment, and (iii) poor electro-optical performance. In order to solve the problems, there are studies on backbone structures of compounds and studies on groups for liquid crystal qualities, combinations of high molecular liquid crystal compounds and low molecular ones, and matrix high molecular liquid crystal compounds wherein low molecular ones are dispersed. However, it is very hard to obtain uniform and stable liquid crystal phases free from phase separation, and furthermore perform high speed response with small viscosity within a wide temperature range including ambient temperature.

Synthesis of a liquid crystal polymer compound having backbone structure of polysiloxane and also having pendant groups where ester type mesogen having an asymmetric carbon is introduced at the terminal of the side-chains was reported (M. Kakimoto, N. F. Cooray and Y. Imai, The 61st annual seminar held by Japan Chemical Society, Mar. 29, 1991), and the compound has been filed as Japanese Patent Application No. Hei 3-276853.

The purpose of the present invention is to develop side-chain liquid crystal polysiloxane compound, and to provide a liquid crystal monomeric compound where a liquid crystal phase readily appears, which is excellent in alignment control, film-formability, durability, heat-stability and compatibility and which is able to be applied to electro-optical liquid crystal elements and recording elements. The present invention further provides a liquid crystal high molecular compound modified with the said monomeric compound.

The first aspect of the present invention resides in that a $CF_3$ or $C_2F_5$ group is directly introduced to the asymmetric carbon atom in place of a pendant methyl group in said compounds by Kakimoto et al. Accordingly, the first of the present invention is to provide a liquid crystal monomeric compound having the following formula:

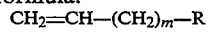

$$CH_2=CH-(CH_2)_m-R \qquad [1]$$

wherein m is an integer of 2 to 20, and R is a group selected from the group consisting of

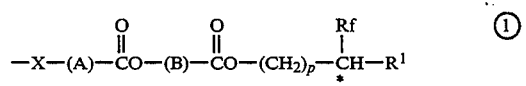

wherein p is 1 or 2, Rf is $CF_3$ or $C_2F_5$, $R^1$ is an alkyl group having 3-18 carbon atoms, * means an optically active carbon atom, (A) and (B) are groups independently selected from the group consisting of

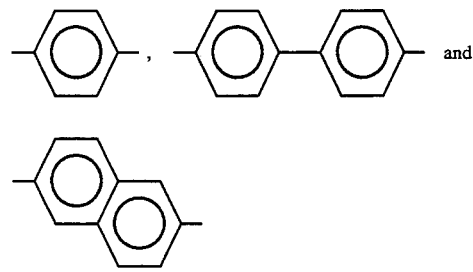

which may be substituted with one or more halogen atoms, and X is —O—, —COO— or a direct linkage, and

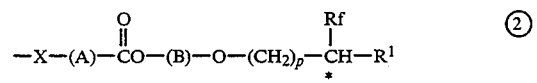

wherein p, Rf, $R^1$, (A), (B), X and * have the same meanings as above.

The second of the present invention is to provide a liquid crystal high molecular compound represented by the following formula:

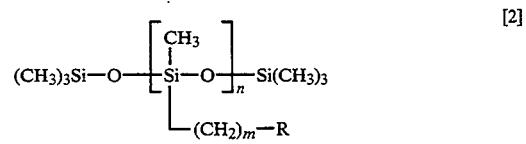

wherein R and m have the same meanings as above, and the inside of [ ] means a recurring unit of the polysiloxane.

There is no limitation on the number of above n, so far as the high molecular compound performs the liquid crystal activity. Normally, n is a number of 1 to 100, preferably 2 to 50, more preferably 3 to 40.

Thus, the liquid crystal polymer compound of the present invention was performed by introducing an asymmetric carbon atom in the molecular structure of the mesogen component to generate perpendicular dipole moment and to exhibit a ferroelectric liquid crystal phase. By giving ferroelectricity to the high molecular liquid crystal polymer, a high speed and large area display became available.

Also, the skeleton structure largely affects to exhibition of liquid crystal phase, the range of the phase transition temperatures and mobility of the side-chain. In the present invention, a flexible polysiloxane structure is used as the skeleton structure to give a high speed response and lower the glass transition point (Tg) to the present compounds, thereby response at ambient temperature being available.

The invention will more fully be illustrated below.

The monomeric compounds represented by the above formula [1] and the liquid crystal high molecular compounds represented by the formula [2] which have the recurring unit are prepared, for example, according to the following synthetic steps.

(1) Preparation of mesogen component:

As shown in the following reaction formulas, 4-benzyloxybenzoyl chloride and optically active 1,1,1-trifluoro-2-octanol are allowed to react in dichloromethane in the presence of a base to synthesize optically active 1,1,1-trifluoro-2-octyl 4-benzyloxybenzoate, which is then debenzylated using palladium carbon in a hydrogen atmosphere to give optically active 1,1,1-trifluoro-2-octyl 4-hydroxybenzoate [a].

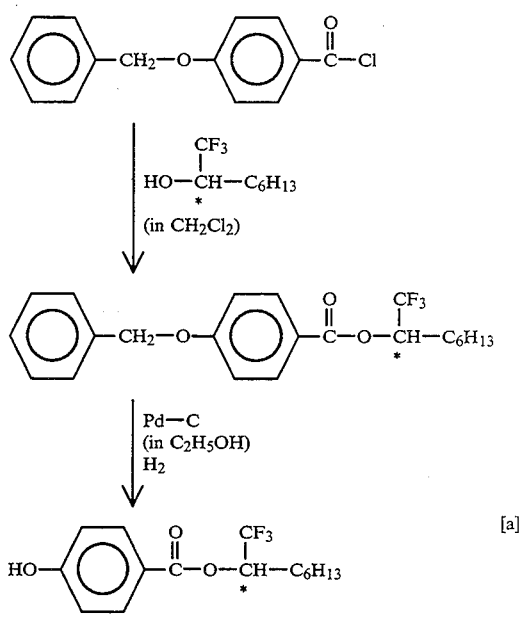

On the other hand, methyl 4-hydroxybiphenyl-4-carboxylate and ω-alkenyl bromide are allowed to react with anhydrous potassium carbonate to give methyl 4-(ω-alkenyloxy)biphenyl-4-carboxylate, which is then subjected to ester hydrolysis in the presence of an alkali to give 4-(ω-alkenyloxy)biphenyl-4'-carboxylic acid [b]. It is then converted to the corresponding acid chloride [b'].

Optically active 1,1,1-trifluoro-2-octyl 4-hydroxybenzoate [a] is allowed to react with the acid chloride [b'] to produce the compound [c], the mesogen component.

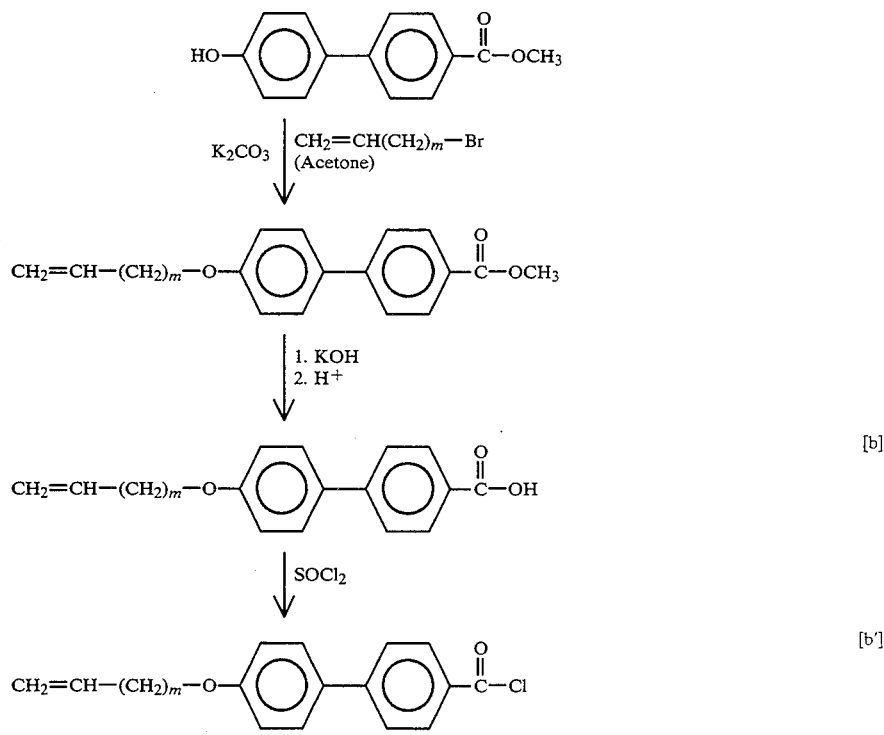

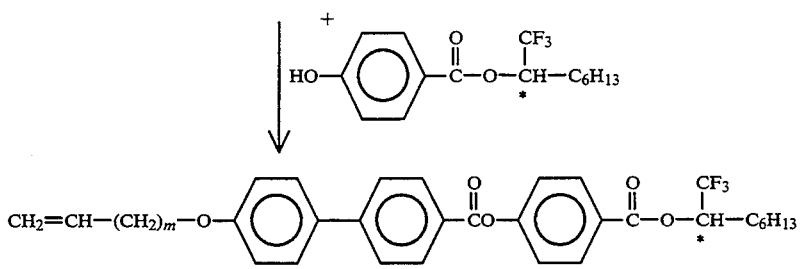

The carbon number, m, at the terminal side chain is an important structural factor relating to the properties of the liquid crystal formed. In the present invention, m is a number within the range of 2 to 20, preferably 2 to 14.

(2) Preparation of the skeleton polymer:

N mole of dichloromethylsilane and M mole of trimethylsilyl chloride are polymerized at a low temperature in tetrahydrofuran (THF) in the presence of concentrated hydrochloric acid to give the desired compound[d].

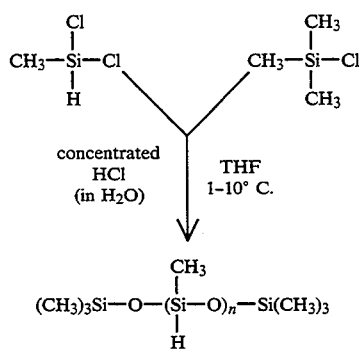

(3) Preparation of the liquid crystal polymer compound:

The liquid crystal polymer compound may be prepared, for example, by subjecting the mesogen component of the formula [c] and the skeleton polysiloxane of the formula [d] to a hydrosilylation reaction. Namely, the compound [c] and the polysiloxane [d] are dissolved in a reaction solvent and the solution is heated to a suitable temperature. Then, the compounds are allowed to combine each other by addition of a platinum catalyst.

Reaction solvents employed in the present invention include ethers, such as dioxane, tetrahydrofuran and diethyl ether; chlorinated solvents, such as dichloromethane, trichloromethane and 1,2-dichloroethane; hydrocarbons, such as n-hexane, heptane, octane, petroleum ether, benzene and toluene; acetone and methyl ethyl ketone. Preferably, dichloromethane, trichloromethane, benzene and toluene are employed.

Platinum catalysts employed in the invention include $PtCl_4$, $H_2PtCl_6 \cdot 6H_2O$, platinum-alcohol complexes and platinum-olefin complexes. Preferred is dicyclopentadienyl-Pt(II) chloride.

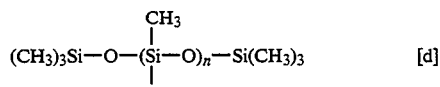

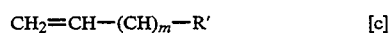

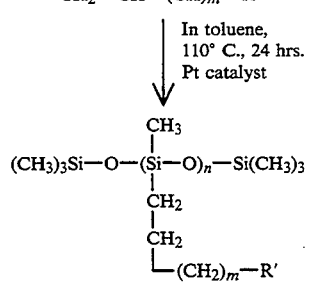

wherein R' is

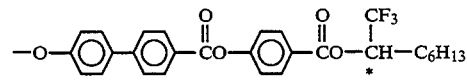

Also, as for the monomeric compounds represented by the above formula [1] and the liquid crystal high molecular compounds represented by the formula [2] which have the recurring unit, a mesogen component of the following formula may be produced in the similar way as above, except that 2-benzyloxynaphthalene-6-carbonyl chloride of the formula [h]is used, in place of 4-benzyloxybenzoyl chloride.

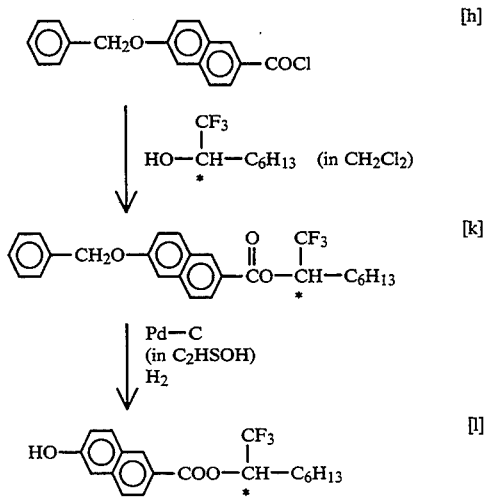

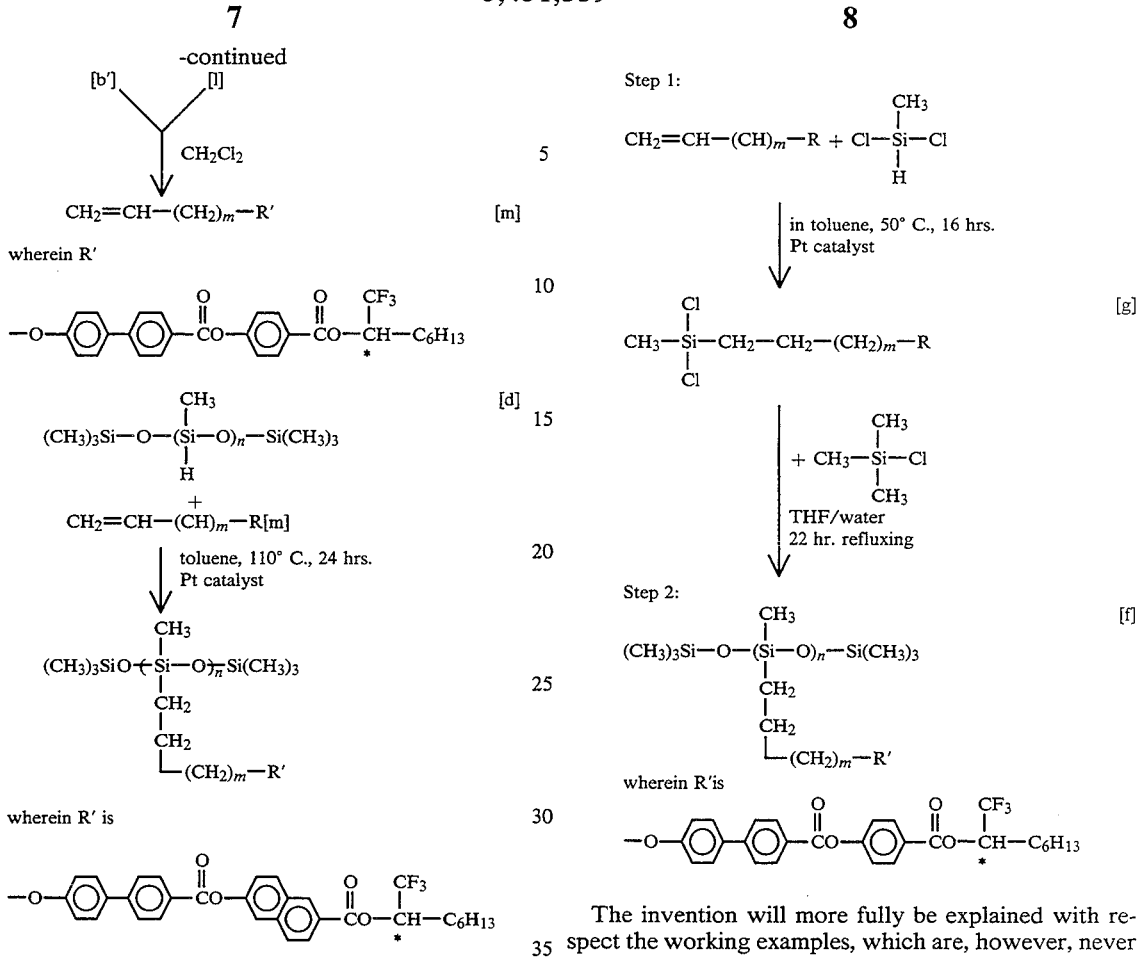

Also, the mesogen components may be prepared according to the following polymerization method.

First step: The compound [c] and dichloromethylsilane are dissolved in a reaction solvent and the solution is heated to a suitable temperature. Then, a platinum catalyst is added thereto for hydrosilylation to give a silylated compound [g] of the compound [c].

Reaction solvents employable for the reaction include ethers, such as dioxane, tetrahydrofuran, and diethyl ether; chlorinated solvents, such as dichloromethane, trichloromethane and 1,2-dichloroethane; hydrocarbons, such as n-hexane, heptane, octane, petroleum ether, benzene and toluene; acetone and methyl ethyl ketone. Preferred are dichloromethane, trichloromethane, benzene and toluene.

Platinum catalysts employable in the reaction include $PtCl_4$, $H_2PtCl_6 \cdot H_2O$, platinum-alcohol complexes and platinum-olefin complexes. Preferred is dicyclopentadienyl-Pt(II) chloride.

Second step: The silylated compound [g] is subjected to polymerization reaction. Thus, N mole of the silylated compound [g] and M mole of trimethylsilyl chloride are polymerized in THF in the presence of water to give the desired compound [f].

The invention will more fully be explained with respect the working examples, which are, however, never construed to limit the invention.

EXAMPLE 1

Synthesis of 4-(1,1,1-trifluoro-2-decyloxycarbonyl)phenyl 4'-(7-octenyloxy)biphenyl-4-carboxylate:

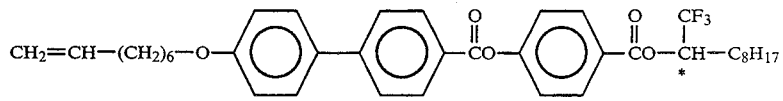

[1] Synthesis of 1,1,1-trifluoro-2-decyl 4-hydroxybenzoate:

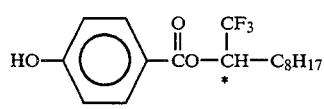

In 10 ml of dichloromethane was dissolved 1.23 g of 4-benzyloxybenzoyl chloride. To the solution was added portionwise a solution of 0.96 g of optically active 1,1,1-trifluoro-2-decanol, $[\alpha]_D^{20} = +23.1$ [c= 0.9453 (wt/vol %), in $CHCl_3$], 0.55 g of dimethylaminopyridine and 0.48 g of triethylamine in 20 ml of dichloromethane, under ice-cooling.

The reaction mixture was brought to room temperature, stood a day and night for reaction, and then poured into ice water. The mixture was extracted with dichloromethane, and the dichloromethane layer was washed sequentially with dilute hydrochloric acid, water, aqueous 1N sodium carbonate solution, and water, and dried over anhydrous magnesium sulfate. The solvent was removed off by distillation to leave a crude product, which was then subjected to toluene-silica gel column chromatography to give 1.71 g of 1,1,1-trifluoro2-decyl 4-benzyloxybenzoate.

The compound was dissolved in 15 ml of ethanol, and 0.36 g of 10% Pd on carbon was added to the solution. The mixture was subjected to hydrogenation in a hydrogenatmosphere to give 1.34 g of the titled 1,1,1-trifluoro-2-decyl 4-hydroxybenzoate.

[2] Synthesis of 4-(7-octenyloxy)biphenyl-4'carboxylic acid:

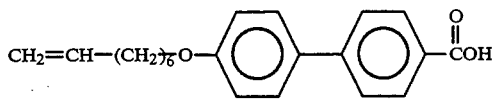

To 50 ml of acetone were added 2.3 g of methyl 4-hydroxybiphenyl-4'-carboxylate, 1.9 g of 7-octenyl bromide and 2.1 g of anhydrous potassium carbonate, and the solution was mildly refluxed for about 8 hours. The solution was poured into 500 ml of ice water, and the mixtue was extracted with dichloromethane. The organic layer was separated. After removal of the solvent, the product was treated with silica gel chromatography to give 3.1 g of an organic matter. The matter was added to 30 ml of methanol containing 1.6 g of KOH dissolved, and the mixture was mildly refluxed for a day and night.

The mixture was poured into 300 ml of ice water, and the isolated colorless powder was separated by filtration, washed with water, neutralized with 1N HCl, collected and dried to give 2.6 g of titled 4-(7-octenyloxy)biphenyl-4'carboxylic acid.

[3] Synthesis of the mesogen component:

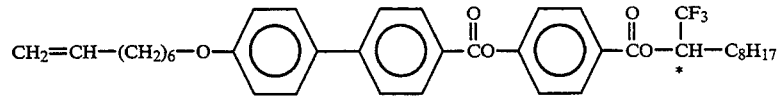

A mixture of 1.3 g of 4-(7-octenyloxy)biphenyl4'-carboxylic acid and an excessive amount of thionyl chloride was refluxed for 6 hours, and then unaltered thionyl chloride was evaporated to leave 4-(7-octenyloxy)-biphenyl-4'-carbonyl chloride.

To a solution of the chloride obtained above in 12.0 ml of dichloromethane was slowly added a solution of 1.34 g of 1,1,1-trifluoro-2-decyl 4-hydroxybenzoate previously synthesized, 0.41 g of triethylamine, and 0.3 g of dimethylaminopyridine in 30 ml of dichloromethane, under ice-cooling. The mixture was stood a day and night at room temperature.

Then, the reaction mixture was poured onto ice water, and extracted with dichloromethane. The dichloromethane layer was washed sequentially with dilute hydrochloric acid, water, aqueous sodium carbonate solution, and then water, and dried over anhydrous sodium sulfate. After removal of the solvent, a crude product was obtained, which was then purified through toluene-silica gel column chromatography to give 1.6 g of optically active desired 4-(1,1,1-trifluoro-2-decyloxycarbonyl)phenyl 4-(7-octenyloxy)biphenyl-4'-carboxylate.

The results from $^1$H-NMR analysis of the resulting compound are as follows:

$^1$H-NMR (CDCl$_3$)δ ppm
6.8–7.3 (12H, m, Ar—H)
5.3–6.0 (2H, m, CHCF$_3$/CH=CH$_2$)
4.8–5.1 (2H, m, CH=CH$_2$)
4.0(2H, t, O—CH$_2$)
1.6–2.2 (6H, m, CH$_2$)
1.1–1.6 (18H, m, CH$_2$)
0.8(3H, t, CH$_3$)

EXAMPLE 2

(1) Synthesis of 4-(1,1,1-trifluoro-2-decyloxycarbonyl)-phenyl 4'-(8-dichloromethylsilyl)octyloxybiphenyl-4'-carboxylate:

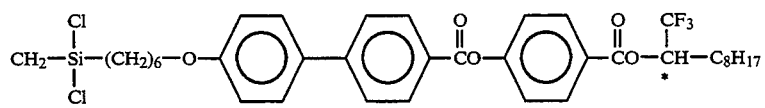

One gram of the mesogen component compound obtained in [3] of Example 1 and 160 μl of dichloromethylsilane were dissolved in dry toluene. Four drops of 0.12 M-THF solution of chloroplatinic acid were added thereto, and the mixture was stirred at 50° C. for 16 hours. After confirming the disappearance of an absorption peak at 2170 cm$^{-1}$ specific to Si—H by infrared absorption spectrum analysis, the reaction mixture was cooled to room temperature. Solid matter was separated by filtration in a nitrogen atmosphere, and the solvent was evaporated to leave a milky yellow, oily, desired compound, which was used for the next polymerization reaction without further purification.

(2) Synthesis of the liquid crystal high molecular compound.

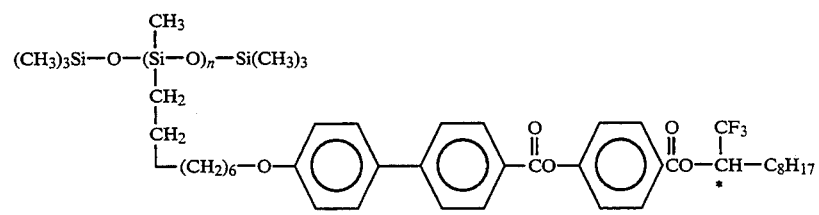

Whole amount of the compound obtained in (1) above was dissolved in 10 ml of THF in a nitrogen atmosphere, and 0.6 ml of distilled water was slowly added dropwise thereto at 0° C. under stirring. After 15 minute stirring, 0.4 ml of pyridine was added thereto, and the mixture was mildly refluxed for 22 hours for polymerization. Then, 20 μl of trimethylchlorosilane was added thereto, and the mixture was mildly refluxed for further 5 hours. After completion of the reaction, an excessive amount of methanol was added to the reaction mixture at room temperature, thereby a polymerized matter being isolated. The isolated matter was again dissolved in THF, and the isolating procedure was repeated several times for purification of the polymerized product. The resulting liquid crystal high molecular compound had physical properties and phase transition temperatures (°C.) observed using a polarizing microscope equipped with a hot stage, as follows:

Number average molecular weight Mn=9,527 Mn/Mw=1.17 (Mw: weight average molecular weight)

TABLE 1

| Measuring temperature (°C.) | Response time (millisecond) |
| --- | --- |
| 62 | 3.5 |
| 57 | 6.0 |
| 47 | 19.2 |

EXAMPLE 3

An electro-optical cell of 3 μm cell thickness having a pair of rubbing-treated polyimide alignment films on Indium-Tin-Oxide electrode substrates was filled with the liquid crystal polymer compound obtained in Example 2 in an isotropic phase to prepare a thin film cell of the liquid crystal high molecular compound.

This liquid crystal cell was arranged to a polarizing microscope equipped with a photomultiplier having two orthogonally crossed polarizing plates so as to make a dark state at 0 V voltage.

The liquid crystal cell was slowly cooled at 0.1°–1.0° C./minute temperature gradient, and pulse voltages of ±40 V were applied at a temperature within the range of 40°–70° C.

The results of measuring the response rate determined from the transmittance are shown in Table 1.

TABLE 1

| Measuring temperature (°C.) | Response time (millisecond) |
| --- | --- |
| 62 | 3.5 |
| 57 | 6.0 |
| 47 | 19.2 |

EXAMPLE 4

(1) Synthesis of 4-(1,1,1-trifluoro-2-decyloxycarbonyl)-phenyl 4'-(5-hexenyloxy)biphenyl-4-carboxylate:

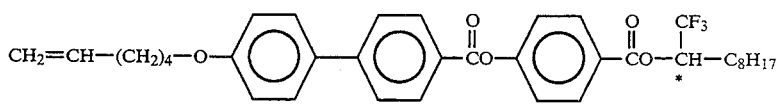

Procedures of Example 1 [2] were repeated except that 1.7 g of 7-hexenyl bromide was used in place of 7-octenyl bromide in Example 1 [2], to give a mesogen component compound.

(2) Synthesis of 4-(1,1,1-trifluoro-2-decyloxycarbonyl)-phenyl 4-(6-dichloromethylsilyl)hexyloxybiphenyl-4'-carboxylate:

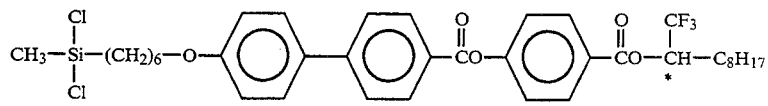

Procedures of Example 2 (1) were repeated except that 1 g of the above mesogen component compound was used in place of the Example 2 (1) mesogen component compound, to give a dichloromethylsilyl derivative having the above formula.

(3) Synthesis of the liquid crystal polymer compound

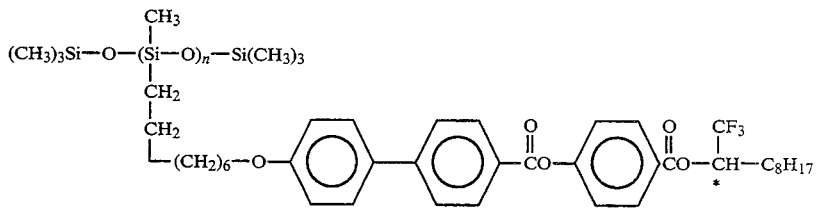

Procedures of Example 2 (2) were repeated except that the whole amount of 4-(1,1,1-trifluoro-2-decyloxycarbonyl)phenyl 4-(6-dichloromethylsilyl)hexyloxybiphenyl-4'-carboxylate was used in place of the dichloromethylsilyl derivative in Example 2 (2), to obtain the above liquid crystal polymer compound.

The resulting compound had physical properties and phase transition temperatures (°C.) observed using a polarizing microscope equipped with a hot stage, as follows:

number average molecular weight Mn =11,000

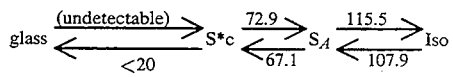

EXAMPLE 5

Synthesis of the liquid crystal polymer compound:

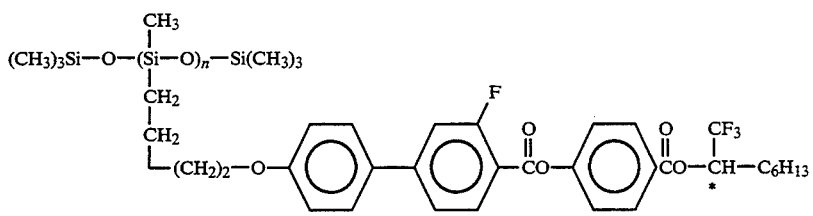

Procedures of Examples 1 and 2 were repeated except that 0.96 g of optically active 1,1,1-trifluoro-2-octanol, 2.3 g of methyl 4-hydroxy-3'-fluorobiphenyl-4'-carboxylate and 1.2 g of 3-butenyl bromide in place of optically active 1,1,1-trifluoro-2-decanol in Example 1 [1], methyl 4-hydroxybiphenyl-4'-carboxylate and 7-octenyl bromide both in Example 1 [2], respectively, to obtain the liquid crystal high molecular compound of the above formula. The resulting compound had physical properties and phase transition temperatures (°C.) observed using a polarizing microscope equipped with a hot stage, as follows:

number average molecular weight Mn=11,800

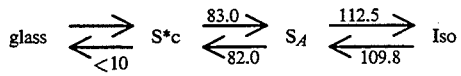

EXAMPLE 6

Synthesis of the liquid crystal polymer compound:

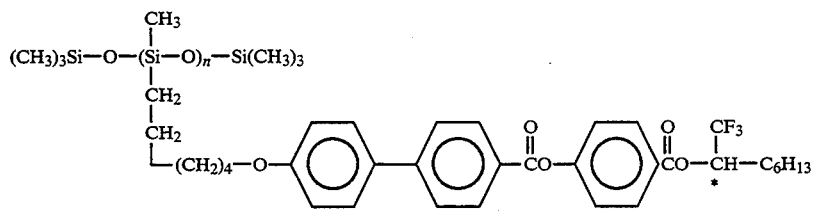

Procedures of Examples 1 and 2 were repeated except that 0.96 g of optically active 1,1,1-trifluoro-2-octanol and 1.9 g of 5-hexenyl bromide in place of optically active 1,1,1-trifluoro-2-decanol in Example 1 [1], and 7-octenyl bromide in Example 1 [2], respectively, to obtain the liquid crystal high molecular compound, which had physical properties and phase transition temperatures (°C.) observed using a polarizing microscope equipped with a hot stage, as follows:

number average molecular weight Mn=4,300

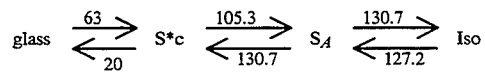

EXAMPLE 7

Electro-optical cells of 3 μm cell thickness each having a pair of rubbing-treated polyimide alignment films on Indium-Tin-Oxide electrode substrates were filled with the liquid crystal high molecular compounds obtained in Example 4, 5 or 6 in an isotropic phase, respectively, to prepare thin film cells of the liquid crystal polymer compounds.

Each liquid crystal cell was arranged to a polarizing microscope with a photomultiplier having two orthogonally crossed polarizing plates so as to make a dark state at 0 V voltage.

The liquid crystal cell was slowly cooled at a 0.1°–1.0° C./minute temperature gradient, and pulse voltages of ±40 V were applied at a temperature within the range of 40°–90° C.

The results of measuring the response rate determined from the transmittance are shown in Tables 2–4.

TABLE 2

| (liquid crystal polymer compound of Example 4) | |
|---|---|
| Measuring temperature (°C.) | Response time (millisecond) |
| 63 | 16 |
| 60 | 32 |
| 55 | 74 |
| 45 | 152 |

TABLE 3

| (liquid crystal polymer compound of Example 5) | |
|---|---|
| Measuring temperature (°C.) | Response time (millisecond) |
| 72 | 1 |
| 62 | 2 |
| 52 | 5 |

TABLE 4

| (liquid crystal polymer compound of Example 6) | |
|---|---|
| Measuring temperature (°C.) | Response time (millisecond) |
| 93 | 0.5 |
| 83 | 0.7 |
| 73 | 2 |

Thus, the novel liquid crystal polymer compounds have so superior film-processability that film displays having a large area and a curved screen are easily produced.

What is claimed is:

1. A liquid crystal monomeric compound represented by the following formula:

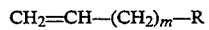

CH$_2$=CH—(CH$_2$)$_m$—R  [1]

wherein m is an integer of 2 to 20 and R is a group selected from the group consisting of

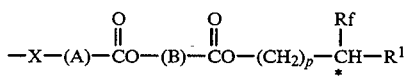 (1)

wherein p is 1 or 2, Rf is CF₃ or CF₂F₅, $R^1$ is an alkyl group having 3-18 carbon atoms, * means an optically active carbon atom, (A) and (B) each is a group independently selected from the group consisting of

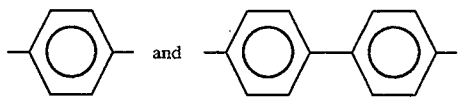

which may be substituted with one or more halogen atoms, and X is —O—, —COO— or a direct linkage, and

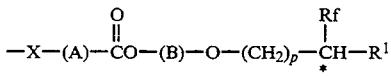 (2)

wherein p, $R^f$, $R^1$, (A), (B), X and * have the same meanings as above.

2. A side-chain liquid crystal polymer compound represented by the following formula:

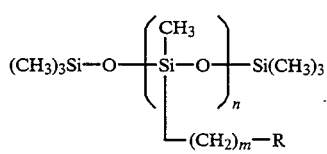 [2]

wherein n is an integer of 1 to 100, m is an integer of 2 to 20 and R is a group selected from the group consisting of

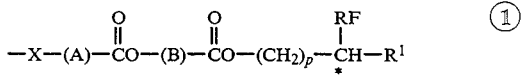 (1)

wherein p is 1 or 2, Rf is CF₃ or CF₂F₅, $R^1$ is an alkyl group having 3-18 carbon atoms, * means an optically active carbon atom, (A) and (B) each is a group independently selected from the group consisting of

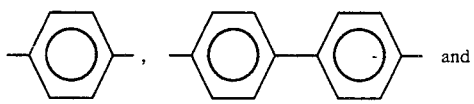 and

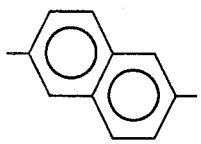

which may be substituted with one or more halogen atoms, and X is —O—, —COO— or a direct linkage, and

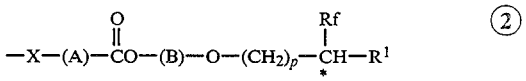 (2)

wherein p, $R^f$, $R^1$, (A), (B), X and * have the same meanings as above.

* * * * *